(12) United States Patent
Kumar et al.

(10) Patent No.: US 10,002,243 B1
(45) Date of Patent: Jun. 19, 2018

(54) SYSTEM AND METHOD FOR POWERING ON ELECTRONIC DEVICES

(71) Applicant: WIPRO LIMITED, Bangalore (IN)

(72) Inventors: Vijay Kumar, Bangalore (IN); Thomas Chittakattu Ninan, Kannur (IN); Shagun Rai, Allahabad (IN)

(73) Assignee: WIPRO LIMITED, Bangalore (IN)

( * ) Notice: Subject to any disclaimer, the term of this patent is extended or adjusted under 35 U.S.C. 154(b) by 0 days. days.

(21) Appl. No.: 15/470,061

(22) Filed: Mar. 27, 2017

(30) Foreign Application Priority Data

Mar. 24, 2017 (IN) .............................. 201741010515

(51) Int. Cl.
| | |
|---|---|
| *G06F 3/043* | (2006.01) |
| *G06F 21/32* | (2013.01) |
| *G01N 29/04* | (2006.01) |
| *G08B 1/08* | (2006.01) |

(52) U.S. Cl.
CPC ............ *G06F 21/32* (2013.01); *G01N 29/045* (2013.01); *G08B 1/08* (2013.01)

(58) Field of Classification Search
CPC ....... G06F 21/32; G06F 3/043; G01N 29/045; G08B 1/08
See application file for complete search history.

(56) References Cited

U.S. PATENT DOCUMENTS

| | | | | |
|---|---|---|---|---|
| 3,614,760 A | * | 10/1971 | Zimmet ................... | G08B 1/08 331/116 M |
| 2001/0047488 A1 | * | 11/2001 | Verplaetse .............. | G06F 21/32 726/5 |
| 2006/0062403 A1 | * | 3/2006 | Yagi ..................... | G01N 29/045 381/91 |
| 2007/0214885 A1 | | 9/2007 | Chernyak et al. | |
| 2008/0136587 A1 | | 6/2008 | Orr | |
| 2011/0096036 A1 | * | 4/2011 | McIntosh ................ | G06F 3/043 345/177 |
| 2012/0116709 A1 | | 5/2012 | Martin et al. | |
| 2014/0111415 A1 | | 4/2014 | Gargi et al. | |
| 2015/0022431 A1 | | 1/2015 | Mahameed | |
| 2015/0260519 A1 | | 9/2015 | Boysel et al. | |

FOREIGN PATENT DOCUMENTS

CN 104503569 4/2015

OTHER PUBLICATIONS

Extended European Search Report issued in the European Patent Office in counterpart European Application No. 17186073.7, dated Feb. 1, 2018, 9 pages.

* cited by examiner

*Primary Examiner* — Nabil Syed
(74) *Attorney, Agent, or Firm* — Finnegan, Henderson, Farabow, Garrett & Dunner LLP

(57) ABSTRACT

This disclosure relates generally to electronic devices, and more particularly to system and method for powering ON electronic devices. In one embodiment, the method comprises receiving a movement pattern provided by a user using the electronic device during a switched OFF state of the electronic device, recording a mechanical movement of a spring-loaded pendulum in response to the movement pattern, validating the mechanical movement against one or more pre-stored patterns, and powering ON the electronic device from the switched OFF state based on a validation. The spring-loaded pendulum is housed within the electronic device.

15 Claims, 12 Drawing Sheets

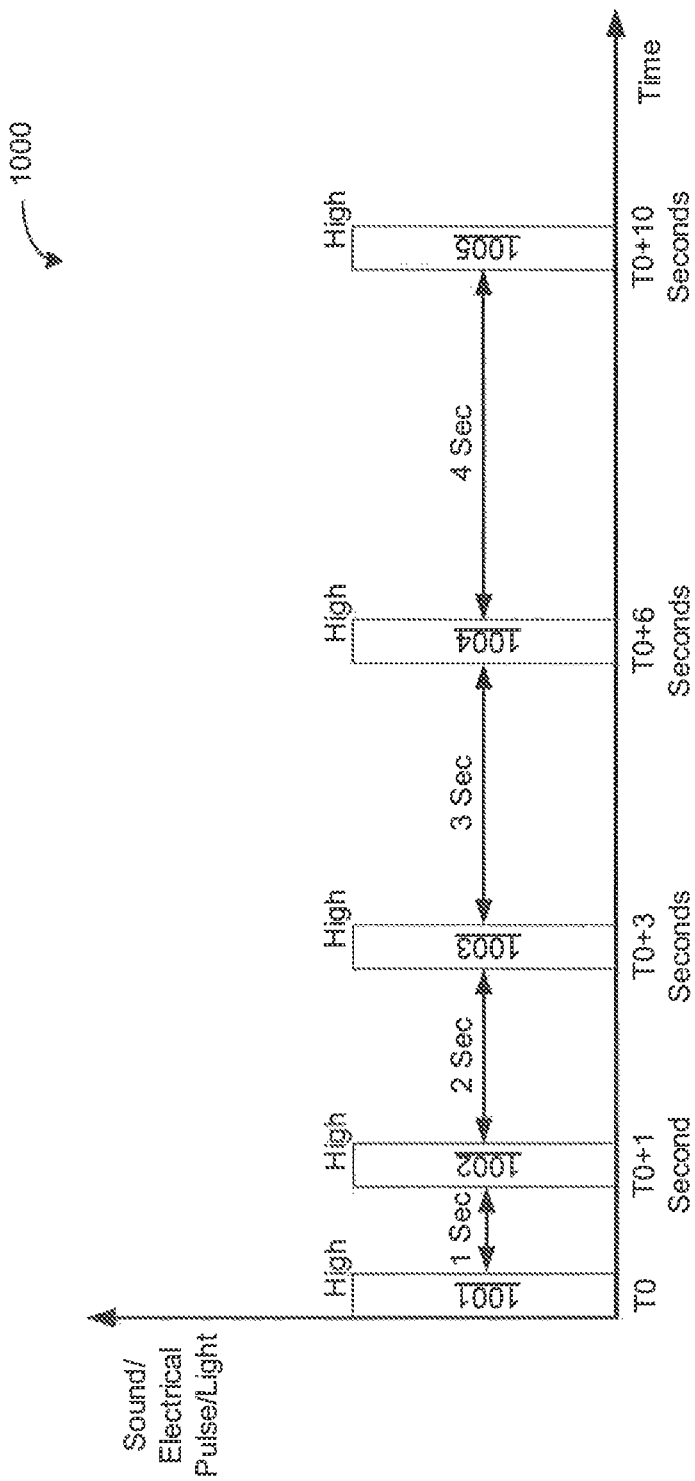

SYSTEM AND METHOD FOR POWERING ON ELECTRONIC DEVICES

TECHNICAL FIELD

This disclosure relates generally to electronic devices, and more particularly to system and method for powering ON electronic devices.

BACKGROUND

Portable electronic devices, including, for example, computers, notebook computers, laptops, tablet devices, cellular telephones, smart phones, have become ubiquitous in today's world and are used extensively by the users in their day to day life. The physical power button of such device may get damaged over time due to such extensive use, and the user may be no longer able to power ON the device with the use of physical power button, thereby rendering the device useless or otherwise causing inconvenience to the user. Since the entire device is shut down during power OFF, it may not be possible to use the device's software to power ON the device. Additionally, the device manufacturers are exploring options to make the devices thinner by doing away with any unnecessary connectors and switches.

SUMMARY

In one embodiment, a method for powering ON an electronic device is disclosed. In one example, the method includes receiving a movement pattern provided by a user using the electronic device during a switched OFF state of the electronic device. The method further includes recording a mechanical movement of a spring-loaded pendulum in response to the movement pattern. The spring-loaded pendulum is housed within the electronic device. The method further includes validating the mechanical movement against one or more pre-stored patterns. The method further includes powering ON the electronic device from the switched OFF state based on a validation.

In one embodiment, a system for powering ON an electronic device is disclosed. In one example, the system includes a spring-loaded pendulum housed within the electronic device. The system further includes at least one processor and a memory communicatively coupled to the at least one processor. The memory stores processor-executable instructions, which, on execution, cause the processor to record a mechanical movement of the spring-loaded pendulum in response to a movement pattern provided by a user using the electronic device during a switched OFF state of the electronic device. The processor-executable instructions, on execution, further cause the processor to validate the mechanical movement against one or more pre-stored patterns. The processor-executable instructions, on execution, further cause the processor to power ON the electronic device from the switched OFF state based on a validation.

In one embodiment, an electronic device is disclosed. In one example, the electronic device includes a spring-loaded pendulum and a microphone housed within a soundproof compartment. The electronic device further includes a set of electrical contacts operable by the spring-loaded pendulum. The electronic device further includes at least one processor and a memory communicatively coupled to the at least one processor. The memory stores processor-executable instructions, which, on execution, cause the processor to record an acoustic pattern via the microphone and an electrical pulse pattern via the set of electrical contacts. The acoustic pattern and the electrical pulse pattern are triggered by a mechanical movement of the spring-loaded pendulum, and the mechanical movement is in response to a movement pattern provided by a user using the electronic device during a switched OFF state of the electronic device. The processor-executable instructions, on execution, further cause the processor to validate the movement pattern by comparing the acoustic pattern with one or more predefined acoustic patterns and by comparing the electrical pulse pattern with one or more predefined electrical pulse patterns. The processor-executable instructions, on execution, further cause the processor to power ON the electronic device from the switched OFF state based on a validation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 10 illustrates an exemplary pre-defined digitized signal pattern employed by the exemplary system for powering ON the electronic device in accordance with some embodiments of the present disclosure.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
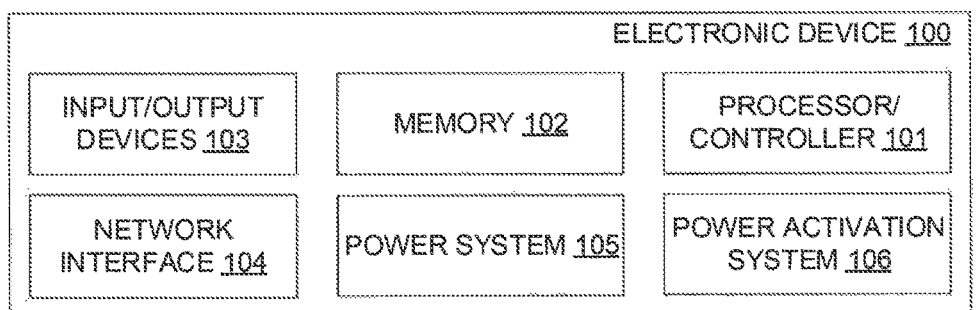
FIG. 1 is a functional block diagram of an exemplary electronic device in accordance with some embodiments of the present disclosure.

Referring now to FIG. 1, a functional block diagram of an exemplary electronic device 100 is illustrated in accordance with some embodiments of the present disclosure. Variations of electronic device 100 may be used for implementing various embodiments of disclosed systems and methods for powering ON the electronic device 100. The electronic device 100 may include, but is not limited to, a tablet, a notebook, a cellular telephone, a smart phone, a portable music player, a portable gaming console, a fitness tracker, and a smart watch. The electronic device 100 includes processors or controllers 101, memory 102, input or output (I/O) devices 103, network interfaces 104, power system 105, and power activation system 106.

The processors or controllers 101 may execute various instructions to carry out various user- or system-generated requests and to carry out various functions of the electronic device 100. A user may include a person using the electronic device 100. The processors or controllers 101 may include, but are not limited to, application-specific integrated circuits (ASICs), digital signal processors (DSPs), Field Programmable Gate Arrays (FPGAs), etc. The memory 102 stores instructions that, when executed by the one or more processors 101, cause the one or more processors 101 to perform various functions of the electronic device 100. For example, the memory 102 may store a set of instructions corresponding to various components and modules of the electronic device 100. The processors or controllers 101 may fetch the instructions from the memory 102 via a wired or wireless communication path, and execute them to perform various functions of the electronic device 100.

The electronic device 100 interacts with the user via the I/O devices 103. For example, the input device 103 may include, but is not limited to, keyboard, mouse, joystick, touch pad, touch screen, microphone, sensor, stylus, etc. Similarly, the output device may include, but is not limited to, a printer, a video display, a speaker, etc. The electronic device 100 further interacts with external devices over a wired or a wireless communication network via the network interface 104. For example, the network interface 104 may include, but is not limited to, a transceiver, a wired network port, and a wireless network port. The external device may include, without limitation, personal computer, server, and other electronic device.

The power system 105 provides power to various components of the electronic device 100 through an internal as well as external power source via a power circuitry. The internal power source may be a fixed or a removal rechargeable battery (e.g., Lithium-ion battery, Nickel metal hydride battery, etc.). The external source may be a direct current source (e.g., portable power bank comprising of rechargeable battery), or an alternating current source (e.g., power socket).

The power activation system 106 activates the power system 105 based on an input from the user so as to power ON the electronic device 100. In some embodiments, the power activation system 106 may include a physical power button and associated power activation circuitry to power ON the electronic device 100. Additionally, in some embodiments, the power activation system 106 may include a mechanical device and associated power activation circuitry to power ON the electronic device 100 in accordance with some embodiments of the present disclosure. For example, the power activation system 106 may power ON the electronic device 100 from a switched OFF state based on a movement pattern provided by a user using the electronic device 100 and without the use of physical power button in accordance with some embodiments of the present disclosure.

In some embodiments, the power activation system 106 includes a processing unit and a memory unit. The memory unit may include a temporary transient (volatile) memory such as random access memory (RAM) and a permanent (non-volatile) memory such as computer readable medium. As will be described in greater detail in conjunction with FIG. 2, the memory unit stores a set of instruction or algorithm which is executed by the processing unit to record a mechanical movement of the mechanical device in response to a movement pattern provided by a user using the electronic device 100 during a switched OFF state of the electronic device 100, to validate the movement pattern against one or more pre-stored patterns, and to power ON the electronic device 100 from the switched OFF state based on a validation.

Figure 2:
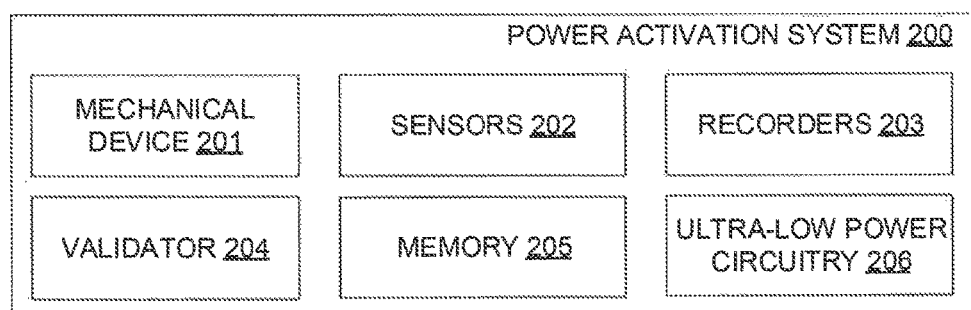
FIG. 2 is a functional block diagram of an exemplary system for powering ON the electronic device in accordance with some embodiments of the present disclosure.

Referring now to FIG. 2, a functional block diagram of an exemplary power activation system 200 for powering ON the electronic device is illustrated in accordance with some embodiments of the present disclosure. The power activation system 200 is analogous to the power activation system 106 implemented by the electronic device 100 of FIG. 1. The power activation system 200 may include various components or modules that perform various functions so as to detect and record a movement pattern provided by the user, validate the movement pattern, and power ON the electronic device based upon a validation. In some embodiments, the power activation system 200 includes mechanical device 201, sensors 202, recorders 203, validator 204, memory 205, and ultra-low power circuitry 206. It should be noted that the various hardware or software based components or modules of the power activation system 200 may be directly connected to each other or may be indirectly connected to each other through one or more intermediate components or modules.

The mechanical device 201 is adapted to mechanically move in response to the movement pattern provided by the user using the electronic device. The user may provide the movement pattern by shaking the electronic device in a systematic pattern. In some embodiments, the mechanical device 201 includes a first contact and a second contact, and the mechanical movement includes a plurality of contacts between the first contact and the second contact as a result of a contemporaneous movement pattern provided by the user. Alternatively, in some embodiments, the mechanical device 201 includes a spring loaded pendulum and the mechanical movement includes a plurality of oscillations of the spring loaded pendulum as a result of a contemporaneous movement pattern provided by the user. In some embodiments, the mechanical device 201 may be housed within an insulated compartment (e.g., air tight compartment, soundproof compartment, dark compartment, etc.) within the electronic device.

As will be appreciated, the movement of the mechanical device 201 triggers a signal pattern corresponding to the mechanical movement. For example, the mechanical movement of the first and the second contact may trigger a signal pattern corresponding to a number of the plurality of contacts, and a time interval between each of the plurality of contacts. Similarly, the mechanical movement of the spring loaded pendulum triggers a signal pattern corresponding to a number of the plurality of oscillations, and a time interval between each of the plurality of oscillations. In some embodiments, the signal pattern may include at least one of acoustic pattern (produced by the first contact coming in contact with the second contact or spring loaded pendulum coming in contact with a tapping surface), electrical pulse pattern (generated by completion of electrical circuit upon first contact or the spring loaded pendulum coming in contact with the second contact or the tapping surface), and light pattern (generated by a light emitting diode (LED) upon completion of electrical circuit).

The sensors 202 detect and capture the signal pattern generated by the mechanical device 201. In some embodiments, the sensors 202 may include at least one of microphones to detect and capture the acoustic pattern, set of electrical contacts to detect and capture electrical pulse patterns, and photodiode to detect and capture light pattern. Thus, the sensors 202 detect and capture the signal pattern (e.g., acoustic pattern, electric pulse pattern, light pattern, etc.) and converts the same into electrical pulse pattern. Additionally, the sensor 202 detects the movement pattern to switch ON the electronic device from a switched OFF state, and triggers the recorder 203 to record the mechanical movement of the mechanical device 201. The recorders 203 receive the captured signal pattern from the sensors 202, processes the captured signal pattern, and temporarily stores the same in the memory 205 for subsequent validation. In some embodiments, the processing of captured signal pattern may include at least one of amplification of the signal pattern, digitization (e.g., analog to digital conversion) of the signal pattern, and conditioning of the signal pattern.

The validator 204 validates the movement pattern by comparing the recorded signal pattern against one or more pre-stored patterns stored in the memory 205. The pre-stored patterns include at least one of pre-defined acoustic patterns, pre-defined electrical pulse pattern, and pre-defined light pattern. As will be appreciated, the pre-stored pattern may be based on type of signal pattern employed and recorded by the power activation system 200. In some embodiments, the pre-stored patterns may be stored in the memory 205 during initial configuration or subsequent re-configuration of the electronic device. In some embodiments, the pre-stored patterns may be configured by the user during switched ON state of the electronic device. Alternatively, in some embodiments, the pre-stored patterns may be configured by the manufacturer of the electronic device 100. For example, when the electronic device 100 is unboxed for the first time after purchase, a default pattern as programmed by the manufacturer and communicated to the user via a user manual or otherwise may be employed to power ON the electronic device. Additionally, the validator 204 generates a control signal to power ON the electronic device 100 from the switched OFF state based on a validation. Thus, if the recorded signal pattern matches one of the pre-stored signal patterns then the validator 204 generates a control signal to power ON the electronic device.

The ultra-low power circuitry 206 supplies ultra-low power during idle or non-active state of the power activation system 200 even when the electronic device is in switched OFF state. Thus, the power activation system 200 is kept in a minimal active state until it detects an attempt to power ON the electronic device. Thus, in some embodiments, the ultra-low power circuitry 206 supplies power to keep the sensors 202 active during the switched OFF state of the electronic device. For example, the ultra-low power circuitry 206 supplies microphone bias voltage to the microphone. Similarly, the ultra-low power circuitry 206 supplies power to the electrical contacts. Additionally, in some embodiments, the ultra-low power circuitry 206 supplies power to a normal power trigger circuitry that triggers supply of normal power to the power activation system 200 upon detection of the signal pattern. For example, the ultra-low power circuitry 206 supplies a reference voltage and operating power to an ultra-low power comparator which triggers a switch upon detection of the signal pattern so as to supply power to all the other component of the power activation system 200. In some embodiments, the ultra-low power circuitry 206 may supply power to the power activation system 200 from the power source (e.g., battery) of the electronic device. Alternatively, the ultra-low power circuitry 206 may supply power to the power activation system 200 from a separate, dedicated power source (e.g., dedicated battery).

It should be noted that the some of the components (e.g., recorder 203, validator 204, etc.) of the power activation system 200 may be implemented in programmable hardware devices such as programmable gate arrays, programmable array logic, programmable logic devices, and so forth. Alternatively, these components may be implemented in software for execution by various types of processors. An identified engine of executable code may, for instance, include one or more physical or logical blocks of computer instructions which may, for instance, be organized as an object, procedure, function, module, or other construct. Nevertheless, the executables of an identified engine need not be physically located together, but may include disparate instructions stored in different locations which, when joined logically together, include the engine and achieve the stated purpose of the engine. Indeed, an engine of executable code could be a single instruction, or many instructions, and may even be distributed over several different code segments, among different applications, and across several memory devices.

As will be appreciated by one skilled in the art, a variety of processes may be employed for powering ON the electronic device. For example, the exemplary electronic device 100 and the exemplary power activation system 200 may facilitate powering ON of the electronic device 100 from the switched OFF state by the processes discussed herein. In particular, as will be appreciated by those of ordinary skill in the art, control logic and/or automated routines for performing the techniques and steps described herein may be implemented by the electronic device 100 and the associated power activation system 200, either by hardware, software, or combinations of hardware and software. For example, suitable code may be accessed and executed by the one or more processors on the electronic device 100 to perform some or all of the techniques described herein. Similarly, application specific integrated circuits (ASICs) configured to perform some or all of the processes described herein may be included in the one or more processors on the electronic device 100.

Figure 3:
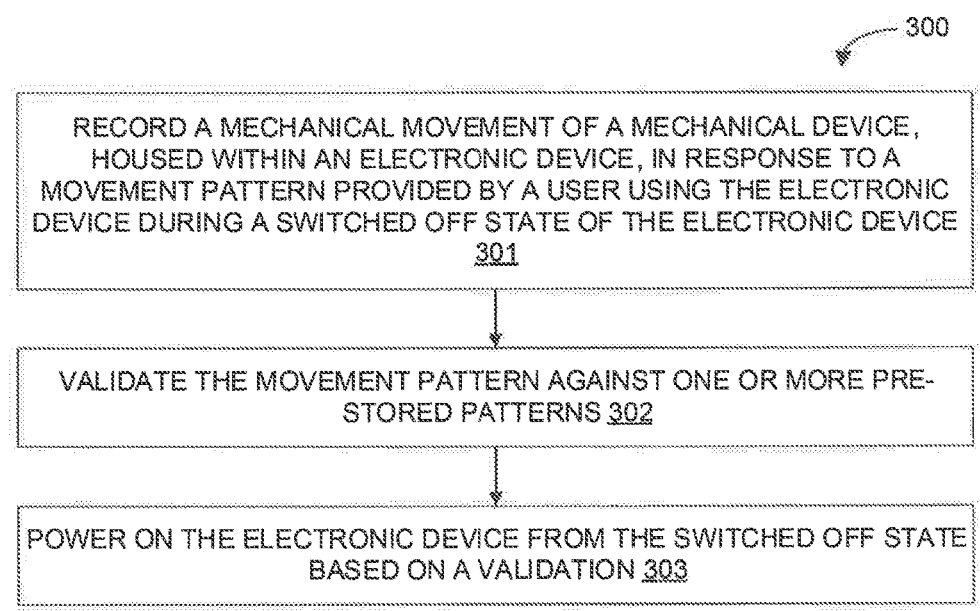
FIG. 3 is a flow diagram of an exemplary process for powering ON the electronic device in accordance with some embodiments of the present disclosure.

For example, referring now to FIG. 3, exemplary control logic 300 for powering ON the electronic device via a power activation system, such as system 200, is depicted via a flowchart in accordance with some embodiments of the present disclosure. As illustrated in the flowchart, the control logic 300 includes the steps of recording a mechanical movement of a mechanical device, housed within the electronic device, in response to a movement pattern provided by a user using the electronic device during a switched OFF state of the electronic device at step 301, validating the movement pattern against one or more pre-stored patterns at step 302, and powering ON the electronic device from the switched OFF state based on a validation at step 303. In some embodiments, the control logic 300 further includes the step of detecting the movement pattern to switch ON the electronic device from a switched OFF state, and triggering the electronic device to record the mechanical movement upon detection. Additionally, in some embodiments, the mechanical device is housed in an insulated compartment within the electronic device. Further, in some embodiments, the movement pattern provided by the user includes shaking of the electronic device.

In some embodiments, the mechanical device includes a first contact and a second contact, and the mechanical movement includes a plurality of contacts between the first contact and the second contact as a result of a contemporaneous movement pattern provided by the user. In such embodiments, the mechanical movement triggers a signal pattern corresponding to a number of the plurality of contacts, and a time interval between each of the plurality of contacts. Additionally, in some embodiments, the mechanical device includes a spring loaded pendulum, and the mechanical movement includes a plurality of oscillations of the spring loaded pendulum as a result of a contemporaneous movement pattern provided by the user. In such embodiments, the mechanical movement triggers a signal pattern corresponding to a number of the plurality of oscillations, and a time interval between each of the plurality of oscillations.

In some embodiments, the mechanical movement triggers an acoustic pattern, and the one or more pre-stored patterns include one or more pre-defined acoustic patterns. In such embodiments, recording the mechanical movement at step 301 includes recording the acoustic pattern using a microphone, and validating the movement pattern at step 302 includes comparing the acoustic pattern with the one or more predefined acoustic patterns. Additionally, in some embodiments, the mechanical movement generates an electrical pulse pattern, and the one or more pre-stored patterns include one or more pre-defined electrical pulse patterns. In such embodiments, recording the mechanical movement at step 301 includes recording the electrical pulse pattern using an electrical contacts, and validating the movement pattern at step 302 includes comparing the electric pulse pattern with the one or more predefined electric pulse patterns. Further, in some embodiments, the mechanical movement triggers a light pattern, and the one or more pre-stored patterns include one or more pre-defined light patterns. In such embodiments, recording the mechanical movement at step 301 includes recording the light pattern using a LED and a photodiode, and validating the movement pattern at step 302 includes comparing the light pattern with the one or more predefined light patterns.

Figure 4:
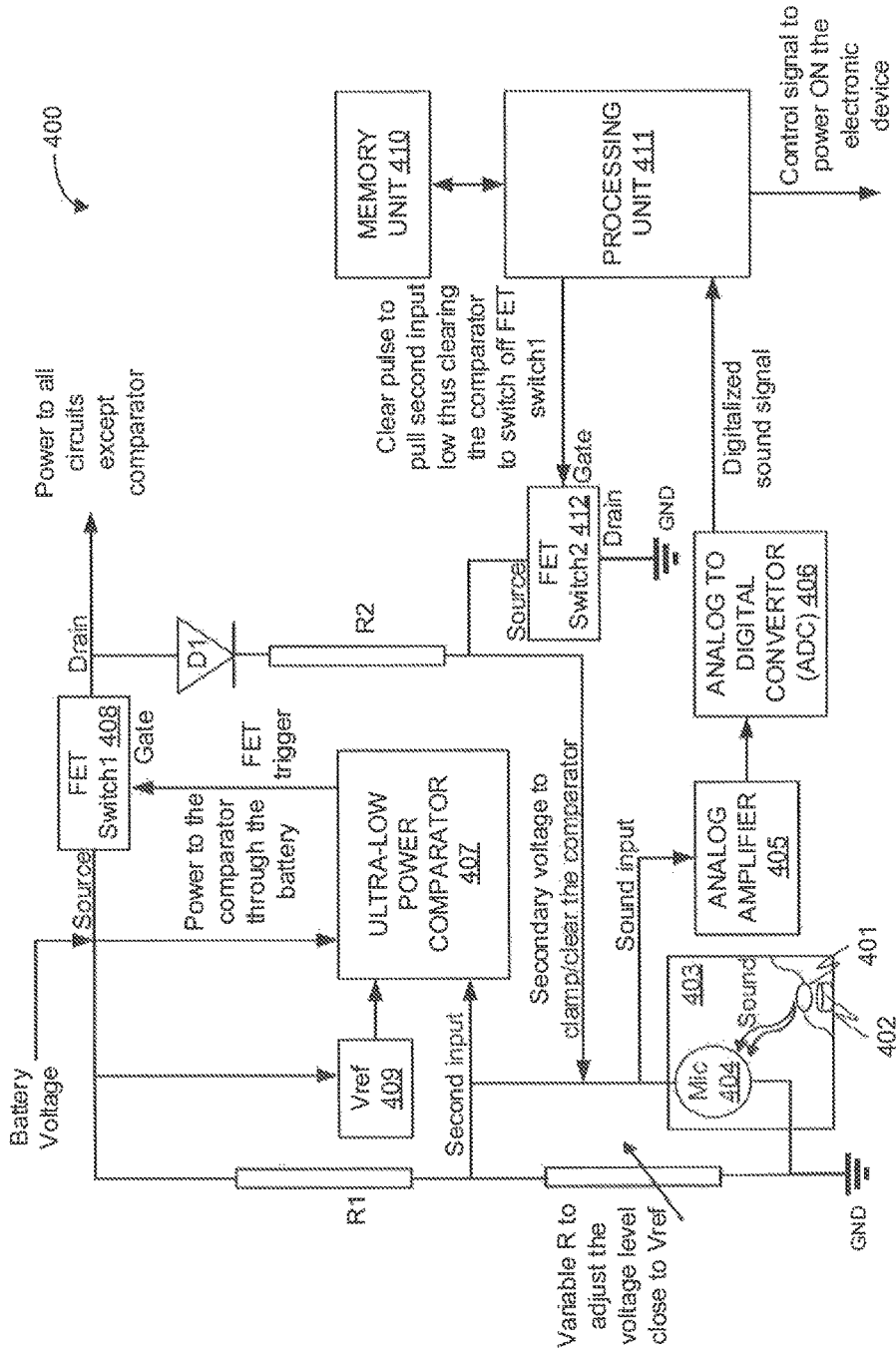
FIG. 4 is a circuit diagram of an exemplary system for powering ON the electronic device based on acoustic pattern in accordance with some embodiments of the present disclosure.

Referring now to FIG. 4, a circuit diagram of an exemplary power activation system 400 for powering ON the electronic device based on acoustic pattern is illustrated in accordance with some embodiments of the present disclosure. The power activation system 400 is analogous to the power activation system 200 described above. The power activation system 400 includes a spring loaded pendulum 401 that vibrates in response to the movement pattern (shaking of the electronic device) provided by the user. The vibrating spring loaded pendulum 401 hits or taps on a tapping surface 402 to produce a sound pattern. The sound pattern, upon validation, may be eventually employed to trigger a control signal for powering ON the electronic device. The spring loaded pendulum 401 and the tapping surface 402 may be disposed within a sound proof compartment 403 so as to prevent any external sound (noise) from entering the power activation system 400 as interference.

The power activation system 400 further includes a microphone 404 for capturing the sound pattern produced by the spring loaded pendulum 401. In some embodiments, the microphone 404 may be a directional microphone placed inside the compartment 403 so as to capture only the sound produced by the pendulum 401. The microphone 404 converts the sound signal to an electrical signal. An analog amplifier 405 amplifies the electrical signal received from the microphone 404. Further, an analog to digital convertor (ADC) 406 converts the amplified analog electrical signal into a digital signal.

An ultra-low power comparator 407 receives the electrical signal from the microphone 404, compares the received electrical signal with a reference voltage (Vref), and triggers a FET switch (FET switch 1) 408 for powering other components of the power activation system 400 based on the comparison. A reference voltage generator 409 generates the reference voltage (Vref) for the ultra-low power comparator 407. Thus, the FET switch 1 408 turns ON the power for all other components of the power activation system 400 upon receiving a trigger from the ultra-low power comparator 407. The trigger is generated when the microphone bias voltage exceeds the reference voltage Vref. A resistor network comprising of resistor R1 and variable resistor R drives a bias voltage for the microphone 404, and maintains the same close (but not equal) to the reference voltage Vref.

A secondary path comprising of diode D1 and resistor R2 provides a secondary voltage to the microphone bias voltage once FET Switch 1 408 is ON. As will be appreciated, this lifts and clamps the microphone bias voltage above the reference voltage Vref, thereby keeping FET Switch 1 408 continuously triggered and consequently keeping all the other components powered.

The memory unit 410 stores one or more pre-defined sound patterns in its non-volatile memory. Additionally, the memory unit 410 may store the recorded sound pattern received from the ADC 406 in its volatile memory. The processing unit 411 receives the digitized sound signals from the ADC 406, and compares the same with the one or more pre-defined sound pattern stored in the memory unit 410. The processing unit 411 further generates a control signal to power ON the electronic device based on the comparison. Thus, if the recorded sound pattern matches with one of the pre-defined sound patterns, then the processing unit 411 generates the control signal. However, if the recorded sound pattern does not match with one of the pre-defined sound patterns, then the processing unit 411 generates a clear pulse to trigger another FET switch (FET switch 2) 412 so as to pull off the secondary lifting voltage on the microphone bias voltage below the reference voltage Vref. This switches OFF the FET switch 1 408 and shuts down most of the components of power activation system 400.

Figure 5A:
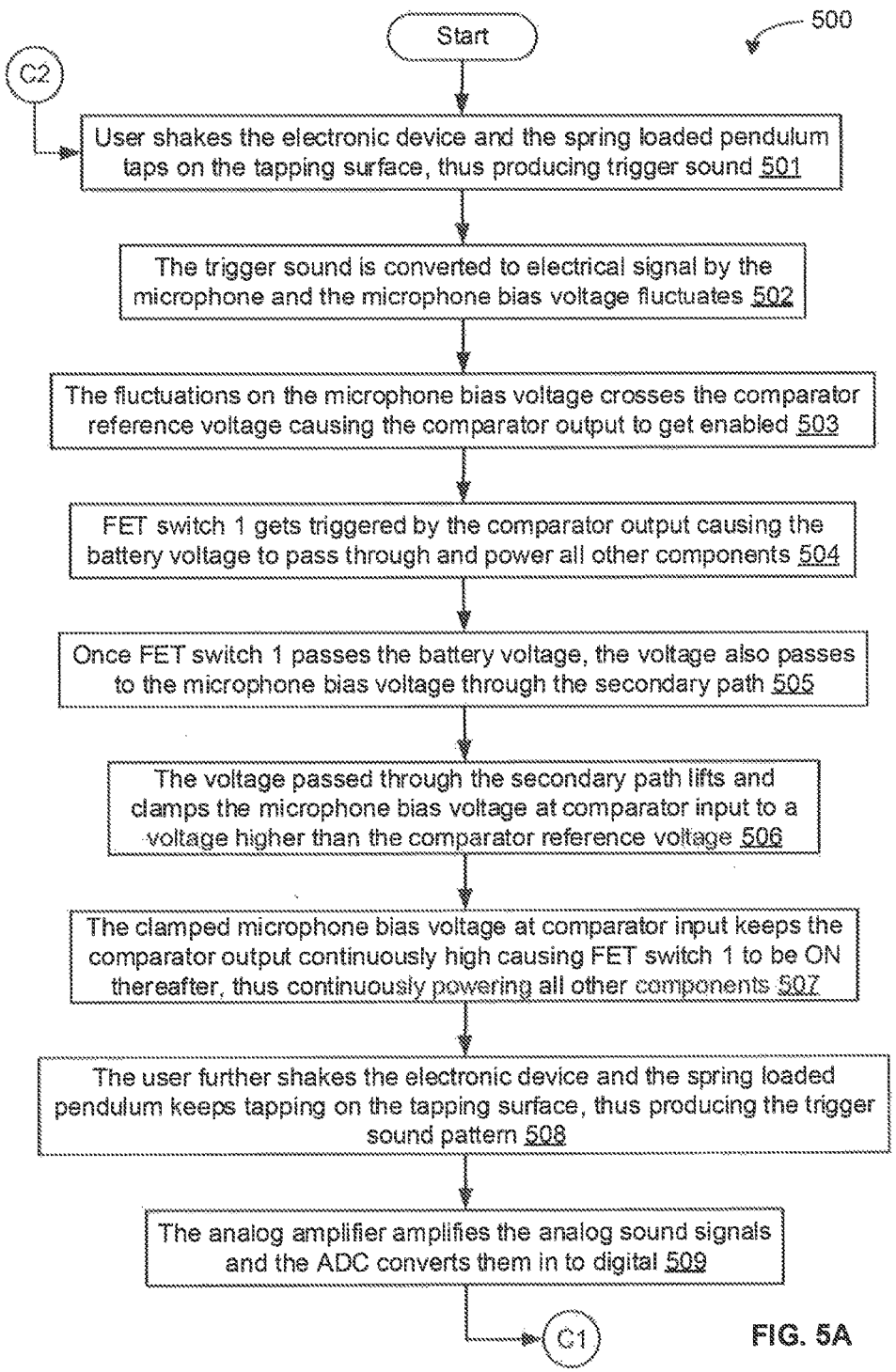
FIGS. 5A and 5B is a flow diagram of a detailed exemplary process implemented by the system of FIG. 4 for powering ON an electronic device based on acoustic pattern in accordance with some embodiments of the present disclosure.
Figure 5B:
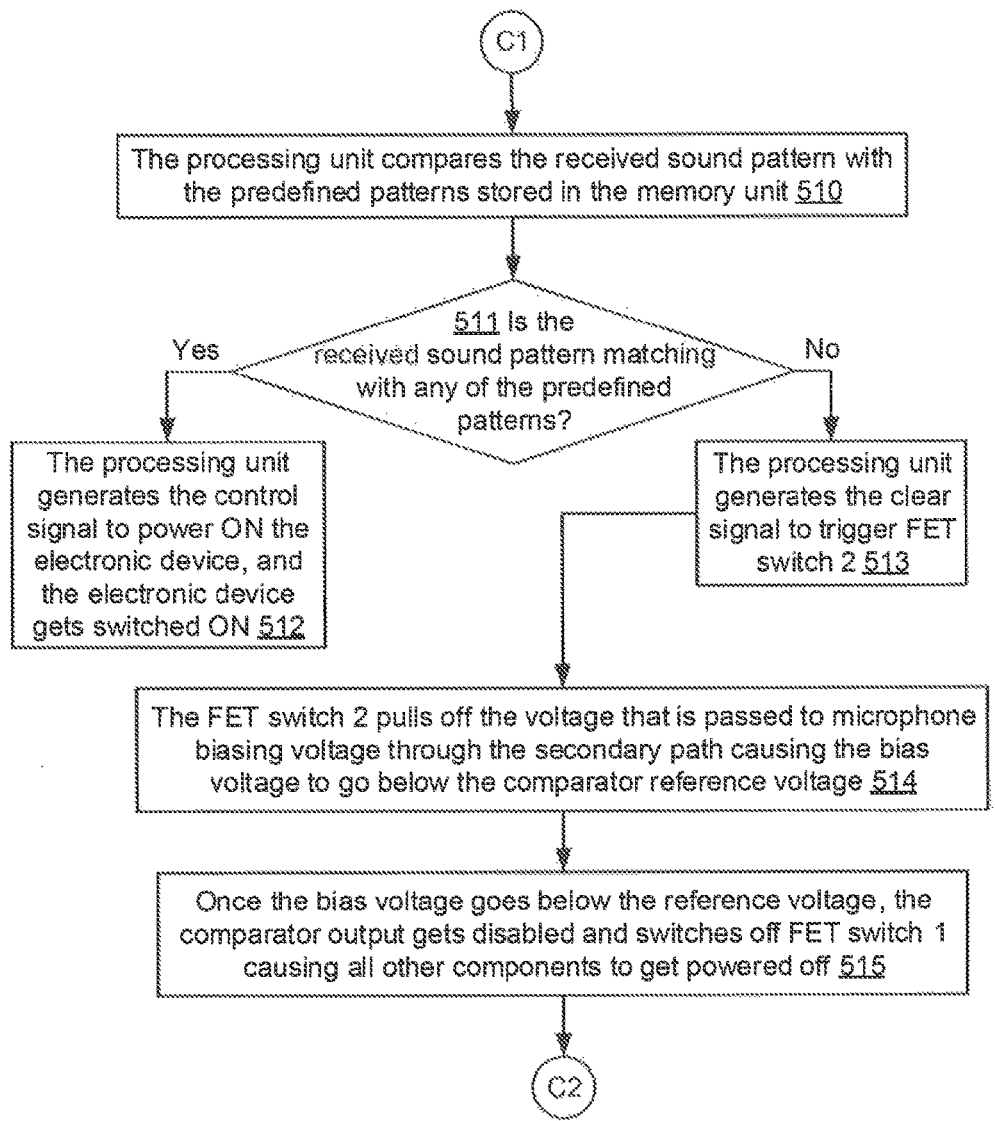

Referring now to FIGS. 5A and 5B, a detailed exemplary control logic 500 implemented by the power activation system 400 for powering ON the electronic device based on acoustic pattern is depicted via a flowchart in accordance with some embodiments of the present disclosure. As illustrated in the flowchart, at step 501, the user shakes the electronic device and consequently the spring loaded pendulum vibrates and taps on the tapping surface, thereby producing trigger sound. At step 502, the trigger sound is converted to electrical signal by the microphone and the microphone bias voltage fluctuates. At step 503, the fluctuations on the microphone bias voltage crosses the comparator reference voltage causing the comparator output to get enabled. At step 504, the FET switch 1 gets triggered by the comparator output, thereby causing the battery voltage to pass through and power all the other components of the power activation system 400. In other words, the initial sound captured by the microphone causes a voltage fluctuation on its bias voltage. As the result, the input voltage at the comparator crosses its reference voltage Vref, thereby enabling the comparator output. The comparator output in turn triggers the FET switch 1, thereby passing the battery power to all the other components.

At step 505, the battery voltage also passes through the secondary path (D1 and R2) to the microphone bias voltage upon triggering of the FET switch 1. At step 506, the voltage passed through the secondary path lifts and clamps the microphone bias voltage at comparator input to a voltage higher than the comparator reference voltage (Vref). At step 507, the clamped microphone bias voltage at comparator input keeps the comparator output to be continuously high, which in turn keeps the FET switch 1 to be continuously ON thereafter, thus continuously powering all the other components.

At step 508, the user further shakes the electronic device and the spring loaded pendulum keeps tapping on the tapping surface, thus producing the trigger sound pattern. At step 509, the analog amplifier amplifies the analog electrical signals (corresponding to the analog sound signals) received from the microphone, and the ADC converts the amplified analog sound signals in to digital sound signals. The ADC then provides the digitalized sound signals to the processing unit.

As will be appreciated, initially only the ultra-low power comparator, the reference voltage generator, and the microphone biasing voltage may be directly powered from the battery. The microphone biasing voltage may be set very close (but not equal) to the reference voltage so that any small fluctuations caused on the bias voltage by the microphone may trigger the comparator, which in turn may trigger the FET switch 1. All the other components of the power activation system 400 may receive power from the battery only when the FET switch 1 is triggered by the comparator, thereby ensuring that the idle (i.e., non-active) state power consumption from the battery is very low.

At step 510, the processing unit compares the received sound pattern with the predefined sound patterns stored in the memory unit. At step 511, the processing unit determines if the received sound pattern matches with one of the pre-defined patterns. If there is a match, at step 512, the processing unit generates the control signal to power ON the electronic device and the electronic device gets switched ON. As will be appreciated, the control signal acts as an alternative signal to the power ON signal received from the physical power button for powering ON the electronic device.

However, if there is no match, at step 513, the processing unit generates the clear signal to trigger FET switch 2. At step 514, the FET switch 2 pulls off the voltage that is passed to microphone biasing voltage through the secondary path, thereby causing the bias voltage to go below the comparator reference voltage. At step 515, once the bias voltage goes below the reference voltage, the comparator output gets disabled, which in turn switches off the FET switch 1 causing all the other components to get powered OFF. As will be appreciated, the above steps may be repeated on shaking the electronic device again.

Figure 6:
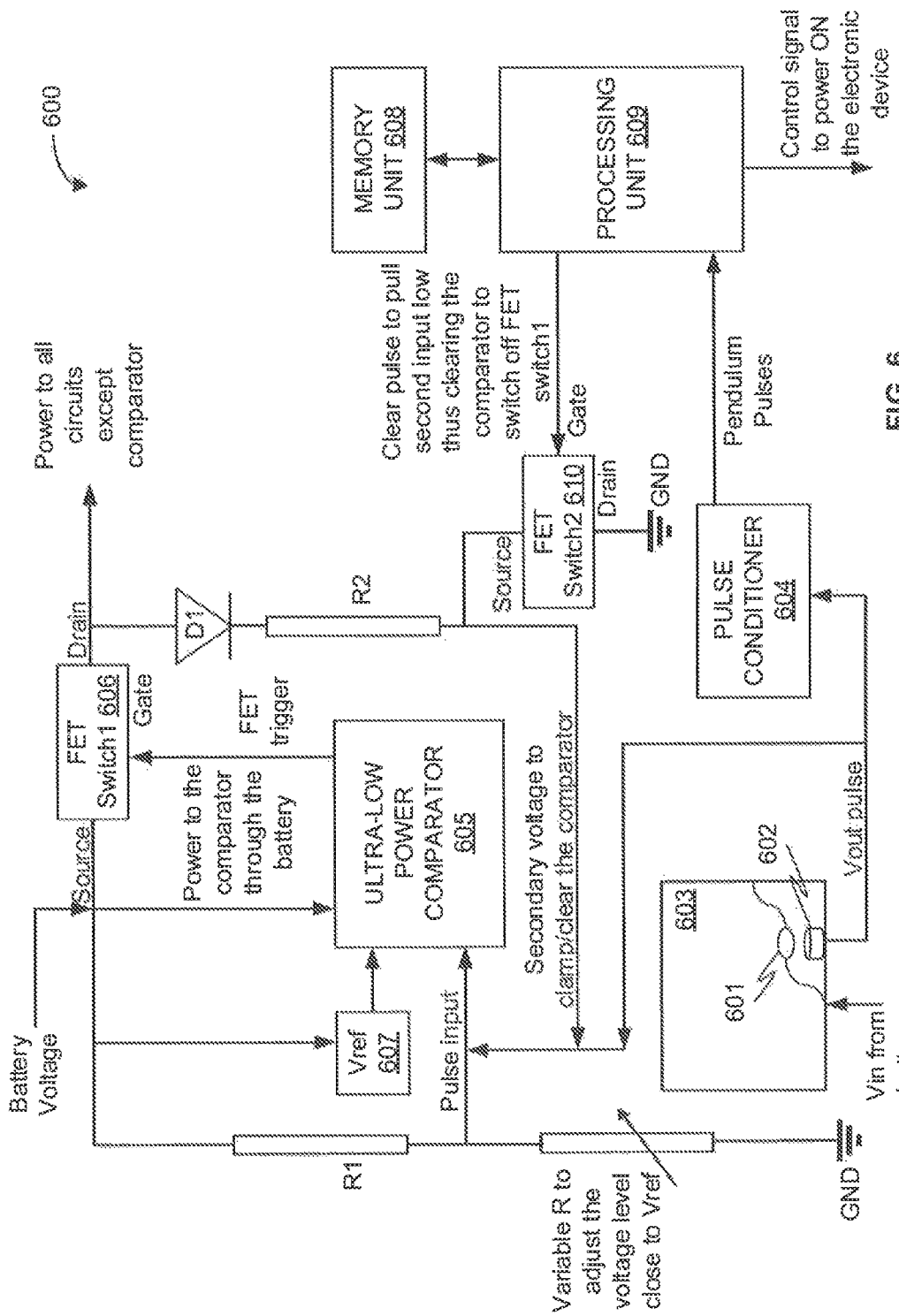
FIG. 6 is a circuit diagram of another exemplary system for powering ON the electronic device based on electric pulse pattern in accordance with some embodiments of the present disclosure.

Referring now to FIG. 6, a circuit diagram of another exemplary power activation system 600 for powering ON the electronic device based on electric pulse pattern is illustrated in accordance with some embodiments of the present disclosure. The power activation system 600 is analogous to the power activation system 200 described above. The power activation system 600 includes a spring loaded pendulum 601 that vibrates in response to the movement pattern (shaking of the electronic device) provided by the user. The vibrating spring loaded pendulum 601 hits or taps on a tapping surface 602. The spring pendulum 601 and the tapping surface 602 are configured to operate a set of electrical contacts so as to generate an electrical pulse pattern. The electrical pulse pattern, upon validation, may be eventually employed to trigger a control signal for powering ON the electronic device. The spring loaded pendulum 601 and the tapping surface 602 may be disposed within an insulated compartment 603 so as to prevent any interference.

The power activation system 600 further includes a pulse conditioner 604 for conditioning the electrical signal generated by the spring loaded pendulum 601 into conditioned digital signal. The conditioning may include de-bouncing of the electrical signal, level shifting of the electrical signal, and so forth. An ultra-low power comparator 605 also receives the electrical signal generated by the spring loaded pendulum 601, compares the received electrical signal with a reference voltage (Vref), and triggers a FET switch (FET switch 1) 606 for powering other components of the power activation system 600 based on the comparison. A reference voltage generator 607 generates the reference voltage (Vref) for the ultra-low power comparator 605. Thus, the FET switch 1 606 turns ON the power for all other components of the power activation system 600 upon receiving a trigger from the ultra-low power comparator 605. The trigger is generated when the electrical voltage generated by the spring loaded pendulum 601 exceeds the reference voltage Vref. A secondary path comprising of diode D1 and resistor R2 provides a secondary voltage to the comparator 605 once FET Switch 1 606 is ON. As will be appreciated, this lifts and clamps the comparator input voltage above the reference voltage Vref, thereby keeping FET Switch 1 606 continuously triggered and consequently keeping all the other components powered.

The memory unit 608 stores one or more pre-defined electrical pulse patterns in its non-volatile memory. Additionally, the memory unit 608 may store the recorded electrical pulse pattern received from the pulse conditioner 604 in its volatile memory. The processing unit 609 receives the conditioned and digitized electrical pulses from the pulse conditioner 604, and compares the same with the one or more pre-defined electrical pulse pattern stored in the memory unit 608. The processing unit 609 further generates a control signal to power ON the electronic device based on the comparison. Thus, if the recorded electrical pulse pattern matches with one of the pre-defined electrical pulse patterns, then the processing unit 609 generates the control signal. However, if the recorded electrical pulse pattern does not match with one of the pre-defined electrical pulse patterns, then the processing unit 609 generates a clear pulse to trigger another FET switch (FET switch 2) 610 so as to pull off the secondary lifting voltage on the comparator input below the reference voltage Vref. This switches OFF the FET switch 1 606 and shuts down most of the components of power activation system 600.

Figure 7A:
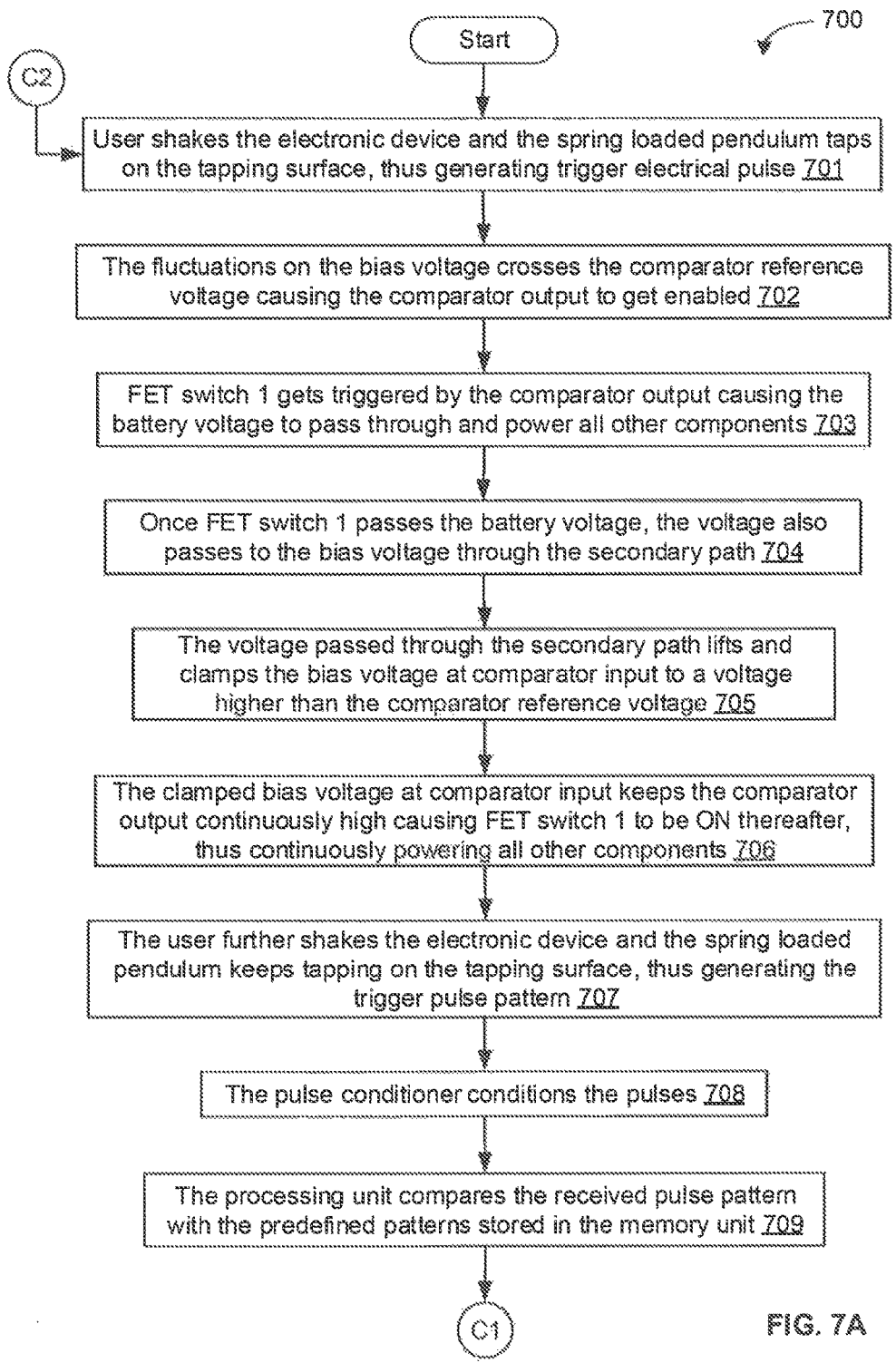
FIGS. 7A and 7B is a flow diagram of a detailed exemplary process implemented by the system of FIG. 6 for powering ON an electronic device based on electric pulse pattern in accordance with some embodiments of the present disclosure.
Figure 7B:
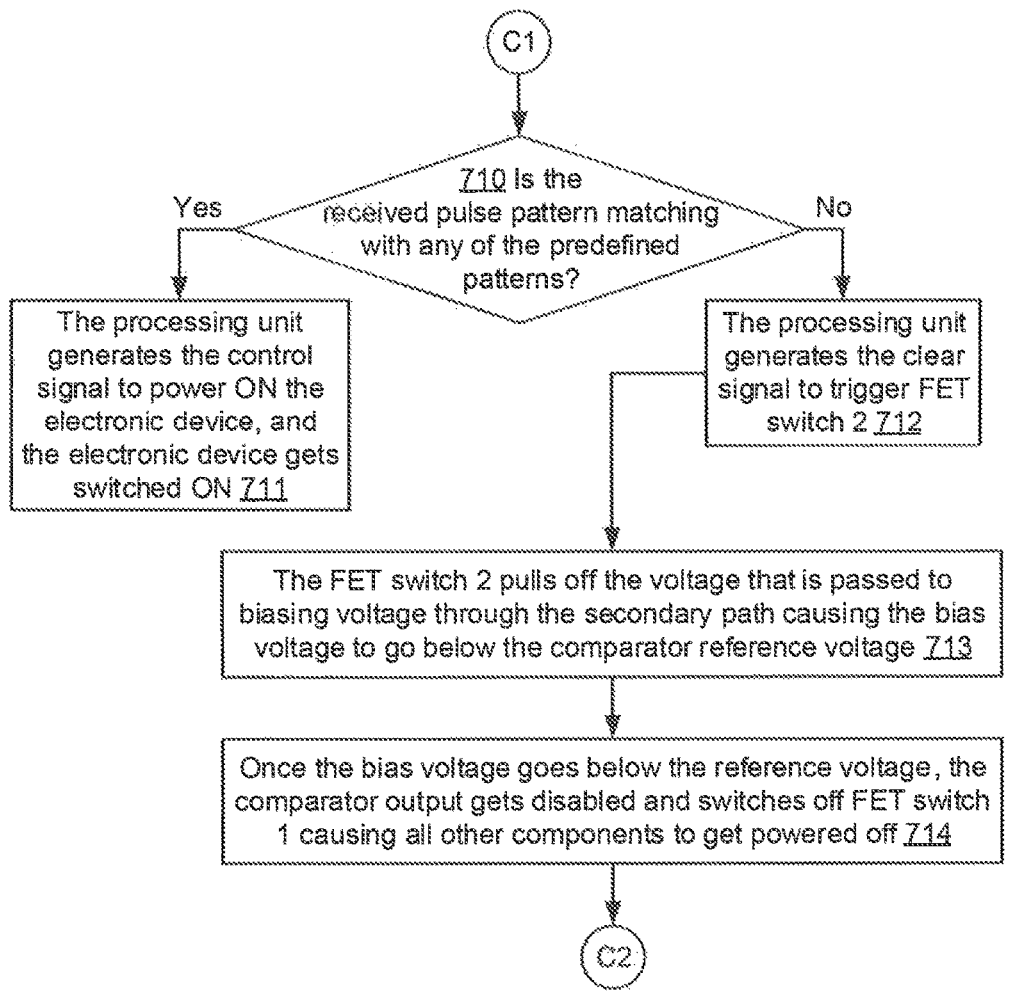

Referring now to FIGS. 7A and 7B, a detailed exemplary control logic 700 implemented by the power activation system 600 for powering ON the electronic device based on electric pulse pattern is depicted via a flowchart in accordance with some embodiments of the present disclosure. As illustrated in the flowchart, at step 701, the user shakes the electronic device and consequently the spring loaded pendulum vibrates and taps on the tapping surface, thereby producing trigger electrical pulse. At step 702, the fluctuations on the bias voltage crosses the comparator reference voltage causing the comparator output to get enabled. At step 703, the FET switch 1 gets triggered by the comparator output, thereby causing the battery voltage to pass through and power all the other components of the power activation system 600. In other words, the initial electrical pulse causes a voltage fluctuation on the bias voltage. As the result, the input voltage at the comparator crosses its reference voltage Vref, thereby enabling the comparator output. The comparator output in turn triggers the FET switch 1, thereby passing the battery power to all the other components.

At step 704, the battery voltage also passes through the secondary path (D1 and R2) to the bias voltage upon triggering of the FET switch 1. At step 705, the voltage passed through the secondary path lifts and clamps the bias voltage at comparator input to a voltage higher than the comparator reference voltage (Vref). At step 706, the clamped bias voltage at comparator input keeps the comparator output to be continuously high, which in turn keeps the FET switch 1 to be continuously ON thereafter, thus continuously powering all the other components.

At step 707, the user further shakes the electronic device and the spring loaded pendulum keeps tapping on the tapping surface, thus generating the trigger electrical pulse pattern. At step 708, the pulse conditioner conditions the electrical pulse signals into digital pulse pattern. The pulse conditioner then provides the digitized electrical pulse pattern to the processing unit.

Again, as will be appreciated, initially only the ultra-low power comparator, the reference voltage generator, voltage at the electrical contacts, and the bias voltage may be directly powered from the battery. The biasing voltage may be set very close (but not equal) to the reference voltage so that any small fluctuations caused on the bias voltage by the electrical contacts may trigger the comparator, which in turn may trigger the FET switch 1. All the other components of the power activation system 600 may receive power from the battery only when the FET switch 1 is triggered by the comparator, thereby ensuring that the idle (i.e., non-active) state power consumption from the battery is very low.

At step 709, the processing unit compares the received electrical pulse pattern with the predefined electrical pulse patterns stored in the memory unit. At step 710, the processing unit determines if the received electrical pulse pattern matches with one of the pre-defined patterns. If there is a match, at step 711, the processing unit generates the control signal to power ON the electronic device and the electronic device gets switched ON. However, if there is no match, at step 712, the processing unit generates the clear signal to trigger FET switch 2. At step 713, the FET switch 2 pulls off the voltage that is passed to biasing voltage through the secondary path, thereby causing the bias voltage to go below the comparator reference voltage. At step 714, once the bias voltage goes below the reference voltage, the comparator output gets disabled, which in turn switches off the FET switch 1 causing all the other components to get powered OFF. As will be appreciated, the above steps may be repeated on shaking the electronic device again.

Figure 8:
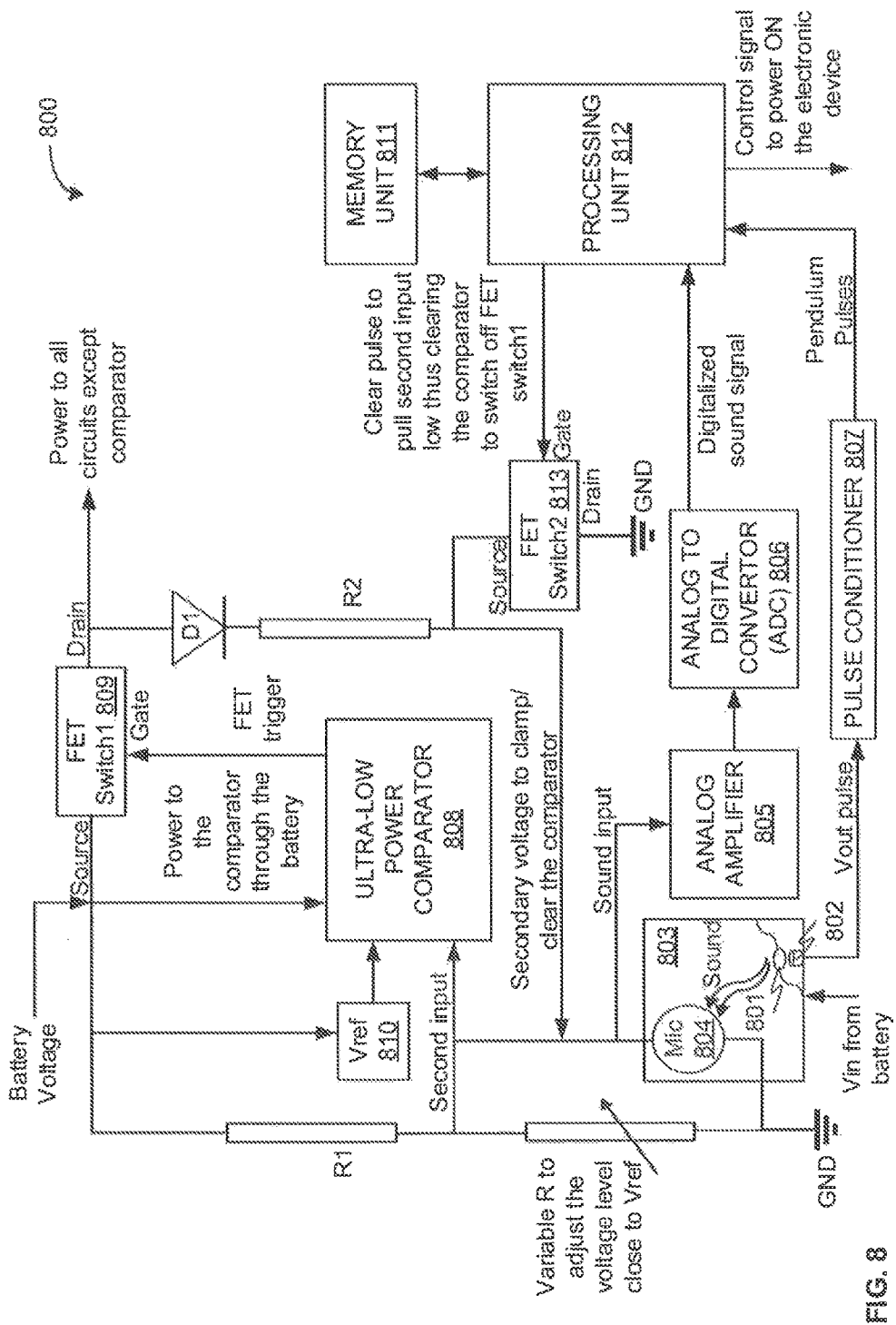
FIG. 8 is a circuit diagram of yet another exemplary system for powering ON the electronic device based on acoustic pattern as well as electric pulse pattern in accordance with some embodiments of the present disclosure.

Referring now to FIG. 8, a circuit diagram of yet another exemplary power activation system 800 for powering ON the electronic device based on acoustic pattern as well as electric pulse pattern is illustrated in accordance with some embodiments of the present disclosure. The power activation system 800 is analogous to the power activation system 200 described above. The power activation system 800 includes a spring loaded pendulum 801 that vibrates in response to the movement pattern (shaking of the electronic device) provided by the user. The vibrating spring loaded pendulum 801 hits or taps on a tapping surface 802 to produce a sound pattern. Additionally, the spring pendulum 801 and the tapping surface 802 are configured to operate a set of electrical contacts so as to generate an electrical pulse pattern. The sound pattern as well as the electrical pulse pattern, upon validation, may be eventually employed to trigger a control signal for powering ON the electronic device. The spring loaded pendulum 801 and the tapping surface 802 may be disposed within an insulated and sound proof compartment 803 so as to prevent any interference from external sound (noise) or otherwise.

The power activation system 800 further includes a microphone 804 for capturing the sound pattern produced by the spring loaded pendulum 801. The microphone 804 converts the sound signal to an electrical signal. An analog amplifier 805 amplifies the electrical signal received from the microphone 804. Further, an analog to digital convertor (ADC) 806 converts the amplified analog electrical signal into a digital signal. Additionally, the power activation system 800 includes a pulse conditioner 807 for conditioning the electrical signal generated by the spring loaded pendulum 801 into conditioned digital signal.

An ultra-low power comparator 808 receives the electrical signal from the microphone 804, compares the received electrical signal with a reference voltage (Vref), and triggers a FET switch (FET switch 1) 809 for powering other components of the power activation system 800 based on the comparison. A reference voltage generator 810 generates the reference voltage (Vref) for the ultra-low power comparator 808. Thus, the FET switch 1 809 turns ON the power for all other components of the power activation system 800 upon receiving a trigger from the ultra-low power comparator 808. The trigger is generated when the microphone bias voltage exceeds the reference voltage Vref. A resistor network comprising of resistor R1 and variable resistor R drives a bias voltage for the microphone 804, and maintains the same close (but not equal) to the reference voltage Vref. A secondary path comprising of diode D1 and resistor R2 provides a secondary voltage to the microphone bias voltage once FET Switch 1 809 is ON. As will be appreciated, this lifts and clamps the microphone bias voltage above the reference voltage Vref, thereby keeping FET Switch 1 809 continuously triggered and consequently keeping all the other components powered.

The memory unit 811 stores one or more pre-defined sound patterns as well as one or more pre-defined electrical pulse pattern in its non-volatile memory. Additionally, the memory unit 811 may store the recorded sound pattern received from the ADC 806 and the recorded electrical pulse pattern received from the pulse conditioner 807 in its volatile memory. The processing unit 812 receives the digitized sound signals from the ADC 806 and digitized electrical pulses from the pulse conditioner 807. The processing unit 812 then compares the digitized sound signals with the one or more pre-defined sound pattern stored in the memory unit 811. The processing unit 812 also compares digitized electrical pulses with the one or more pre-defined electrical pulse pattern stored in the memory unit 811. The processing unit 812 further generates a control signal to power ON the electronic device based on the comparison. As will be appreciated, the electrical pulse pattern in combination with the sound pattern may be employed for more accurately powering ON the electronic device.

Thus, if the recorded sound pattern matches with one of the pre-defined sound patterns and if the recorded electrical pulse pattern matches with one of the pre-defined electrical pulse patterns, then the processing unit 812 generates the control signal. However, if the recorded sound pattern does not match with one of the pre-defined sound patterns, or if the recorded electrical pulse pattern does not match with one of the pre-defined electrical pulse patterns, then the processing unit 812 generates a clear pulse to trigger another FET switch (FET switch 2) 813 so as to pull off the secondary lifting voltage on the microphone bias voltage below the reference voltage Vref. This switches OFF the FET switch 1 809 and shuts down most of the components of power activation system 800.

Figure 9A:
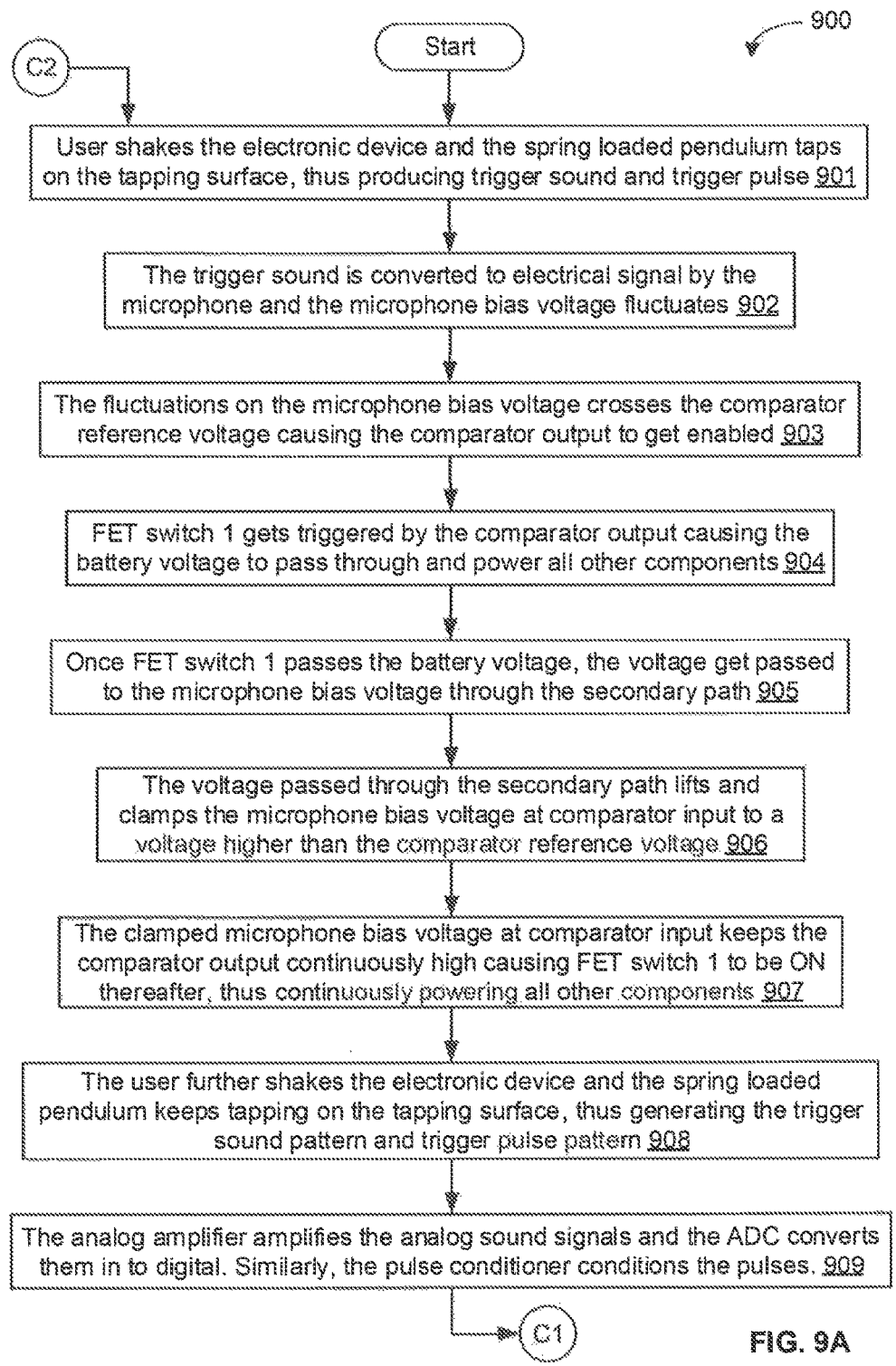
FIGS. 9A and 9B is a flow diagram of a detailed exemplary process implemented by the system of FIG. 8 for powering ON an electronic device based on acoustic pattern as well as electric pulse pattern in accordance with some embodiments of the present disclosure.
Figure 9B:
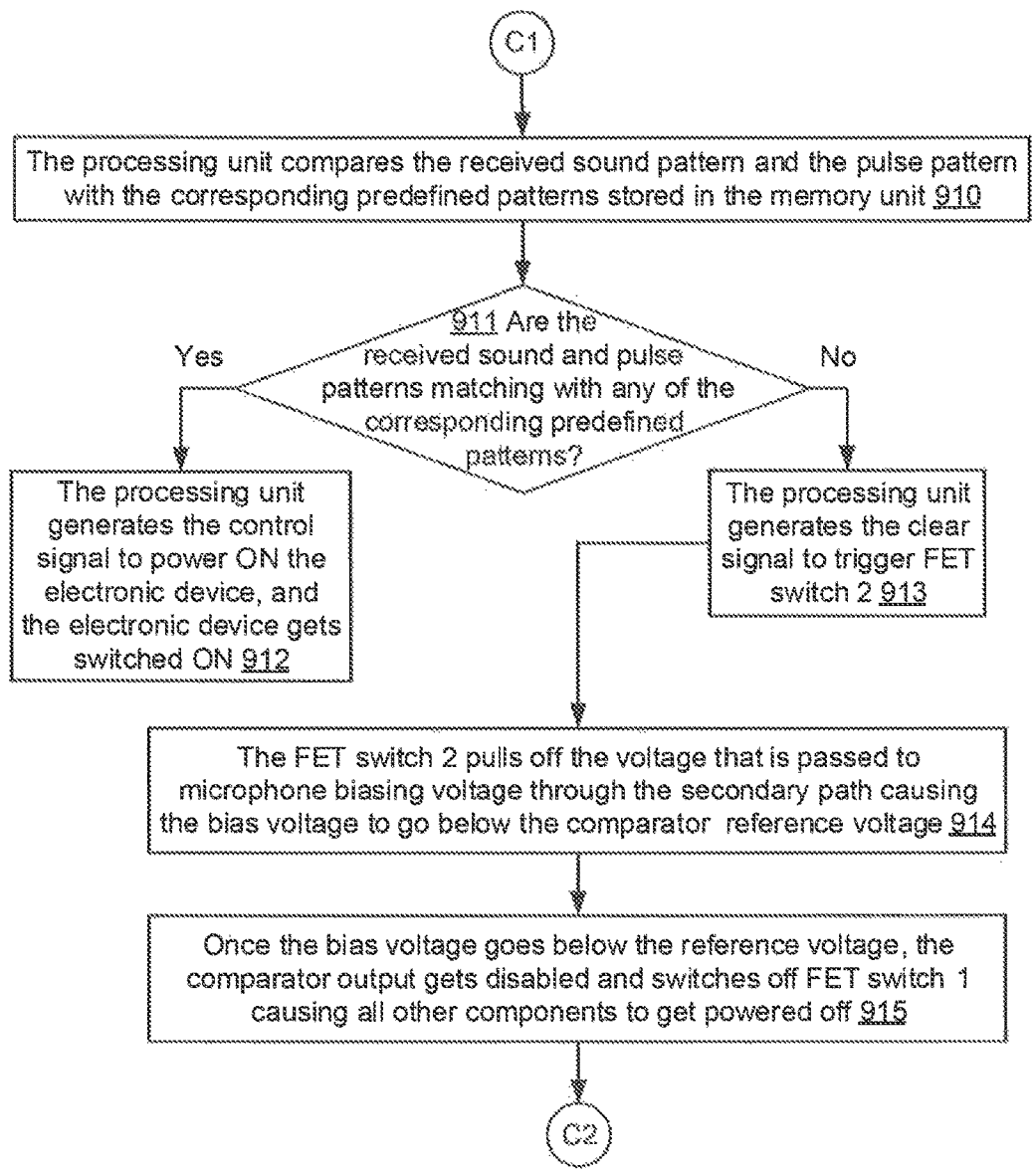

Referring now to FIGS. 9A and 9B, a detailed exemplary control logic 900 implemented by the power activation system 800 for powering ON the electronic device based on acoustic pattern as well as electric pulse pattern is depicted via a flowchart in accordance with some embodiments of the present disclosure. As illustrated in the flowchart, at step 901, the user shakes the electronic device and consequently the spring loaded pendulum vibrates and taps on the tapping surface, thereby producing trigger sound and trigger pulse. At step 902, the trigger sound is converted to electrical signal by the microphone and the microphone bias voltage fluctuates. At step 903, the fluctuations on the microphone bias voltage crosses the comparator reference voltage causing the comparator output to get enabled. At step 904, the FET switch 1 gets triggered by the comparator output, thereby causing the battery voltage to pass through and power all the other components of the power activation system 800.

At step 905, the battery voltage also passes through the secondary path (D1 and R2) to the microphone bias voltage upon triggering of the FET switch 1. At step 906, the voltage passed through the secondary path lifts and clamps the microphone bias voltage at comparator input to a voltage higher than the comparator reference voltage (Vref). At step 907, the clamped microphone bias voltage at comparator input keeps the comparator output to be continuously high, which in turn keeps the FET switch 1 to be continuously ON thereafter, thus continuously powering all the other components.

At step 908, the user further shakes the electronic device and the spring loaded pendulum keeps tapping on the tapping surface, thus generating the trigger sound pattern as well as the trigger electrical pulse pattern. At step 909, the analog amplifier amplifies the analog electrical signals (corresponding to the analog sound signals) received from the microphone, and the ADC converts the amplified analog sound signals in to digital sound signals. The ADC then provides the digitized sound signals to the processing unit. Similarly, the pulse conditioner conditions the electrical pulse signals into digital pulse pattern. The pulse conditioner then provides the digitalized electrical pulse pattern to the processing unit.

At step 910, the processing unit compares the received sound pattern with the pre-defined sound patterns stored in the memory unit. Simultaneously, the processing unit compares the received electrical pulse pattern with the pre-defined electrical pulse patterns stored in the memory unit. At step 911, the processing unit determines if the received sound pattern as well as the received electrical pulse pattern match with any of the corresponding pre-defined patterns. If there is a match for both the patterns, at step 912, the processing unit generates the control signal to power ON the electronic device and the electronic device gets switched ON. However, if there is no match for either of patterns, at step 913, the processing unit generates the clear signal to trigger FET switch 2. At step 914, the FET switch 2 pulls off the voltage that is passed to microphone biasing voltage through the secondary path, thereby causing the bias voltage to go below the comparator reference voltage. At step 915, once the bias voltage goes below the reference voltage, the comparator output gets disabled, which in turn switches off the FET switch 1 causing all the other components to get powered OFF. As will be appreciated, the above steps may be repeated on shaking the electronic device again.

Referring now to FIG. 10, an exemplary pre-defined digitized signal pattern 1000 employed by the exemplary system for powering ON the electronic device is illustrated in accordance with some embodiments of the present disclosure. As stated above, the pre-defined signal pattern 1000 may include at least one of a sound pattern, an electrical pulse pattern, and a light pattern. For example, as illustrated, in case of a sound pattern, a 'high' indicates the occurrence of a tapping sound via the pendulum while the user is moving the device. Similarly, in case of an electrical pulse pattern, the 'high' indicates the occurrence of an electrical pulse via the pendulum electrical contacts while the user is moving the device. Similarly, in case of a light pattern, the 'high' indicates the occurrence of a light pulse (e.g., lighting of an LED) via the pendulum electrical contacts and a connected LED while the user is moving the device. As will be appreciated, in some embodiments, the occurrence of the tapping sound, electrical pulse, or light pulse may be indicated by a 'low' rather than the 'high'. Further, as stated above, the pre-defined signal pattern may be structured with different intervals. For example, as illustrated, the pre-defined signal pattern 1000 includes a first trigger 1001 at T0, a second trigger 1002 at T0+1 second (i.e., 1 second after the first trigger), a third trigger 1003 at T0+3 seconds (i.e., 2 seconds after the second trigger), a forth trigger 1004 at T0+6 seconds (i.e., 3 seconds after the third trigger), and a fifth trigger 1005 at T0+10 seconds (i.e., 4 seconds after the fourth trigger).

As will be also appreciated, at least a portion of the above described techniques may take the form of computer or controller implemented processes and apparatuses for practicing those processes. The disclosure can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Further, as will be appreciated by those skilled in the art, the techniques described in the various embodiments discussed above provide for a mechanism for powering ON the electronic device from a completely switched OFF state without the use of physical power button and/or without the use of device's primary software (that is accessible only during a switched ON state of the device). The techniques described in the embodiments discussed above, provide a dedicated power activation circuitry comprising of hardware as well as software modules so as to power ON the electronic device from a completely switched OFF state without using the physical power button.

As will be appreciated by those skilled in the art, existing techniques provide for detection of user input (e.g., touch, voice command, gesture, etc.) and processing of input typically through embedded sensors (e.g., touch screen, accelerometer, etc.) and associated software. However, since the electronic device as well as all the associated circuitries in the electronic device are completely powered OFF during the switched OFF state of the electronic device, they cannot be employed to provide for a mechanism to power ON the electronic device from a completely switched OFF state.

Additionally, the techniques described in the various embodiments discussed above provide for an optimized power consumption by the power activation system. The power consumption of the power activation circuitry during a switched OFF state of the electronic device is kept at minimum (i.e. powering only ultra-low power comparator, reference voltage generator, etc.) during the switched OFF state. The other components of the power activation circuitry are powered only upon the detection trigger signals.

The specification has described system and method for powering ON electronic devices. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for powering ON an electronic device, the method comprising:
    receiving a movement pattern provided by a user using the electronic device during a switched OFF state of the electronic device;
    recording a mechanical movement, wherein recording the mechanical movement includes recording, via a microphone housed within a soundproof compartment with a spring-loaded pendulum, an acoustic pattern triggered by the spring-loaded pendulum in response to the movement pattern, wherein the spring-loaded pendulum is housed within the electronic device;
    validating the mechanical movement by, at least, comparing the acoustic pattern with one or more predefined acoustic patterns; and
    powering ON the electronic device from the switched OFF state based on a validation.

2. The method of claim 1, wherein the mechanical movement generates an electrical pulse pattern, and wherein the one or more pre-stored patterns correspond to one or more pre-defined electrical pulse patterns.

3. The method of claim 2, wherein validating the mechanical movement comprises comparing the electrical pulse pattern with the one or more predefined electrical pulse patterns.

4. The method of claim 1, wherein the mechanical movement triggers a light pattern, and wherein the one or more pre-stored patterns correspond to one or more pre-defined light patterns.

5. The method of claim 4, wherein validating the mechanical movement comprises comparing the light pattern with the one or more predefined light patterns.

6. The method of claim 1, wherein the mechanical movement comprises a number of a plurality of oscillations of the spring loaded pendulum, and a time interval between each of the plurality of oscillations.

7. The method of claim 1, wherein recording the mechanical movement further comprises recording at least one of an electrical pulse pattern using a set of electrical contacts and a light pattern using a light emitting diode and a photodiode.

8. The method of claim 1, wherein the movement pattern provided by the user comprises shaking of the electronic device.

9. A system for powering ON an electronic device, the system comprising:
    a spring-loaded pendulum and a microphone housed within a soundproof compartment of the electronic device;
    at least one processor; and
    a computer-readable medium storing instructions that, when executed by the at least one processor, cause the at least one processor to perform operations comprising:
        recording a mechanical movement of the spring-loaded pendulum in response to a movement pattern provided by a user using the electronic device during a switched OFF state of the electronic device, wherein recording the mechanical movement includes recording, via the microphone, an acoustic pattern triggered by the spring-loaded pendulum in response to the movement pattern;
        validating the mechanical movement by, at least, comparing the acoustic pattern with one or more pre-defined acoustic patterns; and
        powering ON the electronic device from the switched OFF state based on a validation.

10. The system of claim 9, wherein the mechanical movement generates an electrical pulse pattern, wherein the one or more pre-stored patterns correspond to one or more pre-defined electrical pulse patterns, and wherein validating the mechanical movement comprises comparing the electrical pulse pattern with the one or more predefined electrical pulse patterns.

11. The system of claim 9, wherein the mechanical movement triggers a light pattern, wherein the one or more pre-stored patterns correspond to one or more pre-defined light patterns, and wherein validating the mechanical movement comprises comparing the light pattern with the one or more predefined light patterns.

12. The system of claim 9, wherein the mechanical movement comprises a number of a plurality of oscillations of the spring loaded pendulum, and a time interval between each of the plurality of oscillations.

13. The system of claim 9, wherein recording the mechanical movement further comprises recording at least one of an electrical pulse pattern using a set of electrical contacts and a light pattern using a light emitting diode and a photodiode.

14. The system of claim 9, wherein the movement pattern provided by the user comprises shaking of the electronic device.

15. An electronic device, comprising:
a spring-loaded pendulum and a microphone housed within a soundproof compartment;
a set of electrical contacts operable by the spring-loaded pendulum;
at least one processor; and
a computer-readable medium storing instructions that, when executed by the at least one processor, cause the at least one processor to perform operations comprising:
recording an acoustic pattern via the microphone and an electrical pulse pattern via the set of electrical contacts, wherein the acoustic pattern and the electrical pulse pattern are triggered by a mechanical movement of the spring-loaded pendulum, and wherein the mechanical movement is in response to a movement pattern provided by a user using the electronic device during a switched OFF state of the electronic device;
validating the movement pattern by comparing the acoustic pattern with one or more predefined acoustic patterns and by comparing the electrical pulse pattern with one or more predefined electrical pulse patterns; and
powering ON the electronic device from the switched OFF state based on a validation.

* * * * *